United States Patent [19]

Sakaguchi et al.

[11] Patent Number: 4,536,466

[45] Date of Patent: Aug. 20, 1985

[54] HEAT DEVELOPABLE ELEMENT WITH STABILIZER

[75] Inventors: Yukihiko Sakaguchi; Toshiaki Aono; Shinsaku Fujita, all of Kanagawa, Japan

[73] Assignee: Fuji Photo Film Co., Ltd., Kanagawa, Japan

[21] Appl. No.: 594,511

[22] Filed: Mar. 29, 1984

[30] Foreign Application Priority Data

Mar. 30, 1983 [JP] Japan .................. 58-54166

[51] Int. Cl.³ .................. G03C 1/40; G03C 5/54; G03C 1/34
[52] U.S. Cl. .................. 430/203; 430/219; 430/372; 430/351; 430/559; 430/607; 430/617; 430/619
[58] Field of Search .................. 430/203, 219, 223, 617, 430/619, 351, 551, 372, 607, 559

[56] References Cited

U.S. PATENT DOCUMENTS

| | | | |
|---|---|---|---|
| 2,735,765 | 2/1956 | Loria et al. | 430/551 |
| 4,124,387 | 11/1978 | Kohrt | 430/203 |
| 4,254,216 | 3/1981 | Uchida et al. | 430/372 |
| 4,268,621 | 5/1981 | Ogi et al. | 430/551 |
| 4,401,754 | 8/1983 | Suzuki et al. | 430/607 |
| 4,430,415 | 2/1984 | Aono et al. | 430/351 |
| 4,463,079 | 7/1984 | Naito et al. | 430/223 |

*Primary Examiner*—Richard L. Schilling
*Attorney, Agent, or Firm*—Sughrue, Mion, Zinn, Macpeak & Seas

[57] ABSTRACT

A method of forming an image comprising heating a light-sensitive material having at least a light-sensitive silver halide, a binder and a dye releasing redoc compound which is capable of reducing the light-sensitive silver halide and is capable of reacting with the light-sensitive silver halide by heating to release a hydrophilic dye on a support, under the condition substantially free from water after or simultaneously with imagewise exposure, in the presence of a compound represented by the general formula (A) described below to form imagewise a mobile dye.

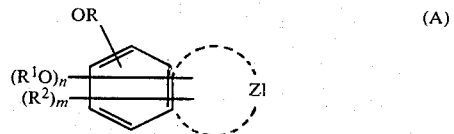

wherein R represents an alkyl group, a cycloalkyl group, an aryl group or an aralkyl group; $R^1$ represents an alkyl group, a cycloalkyl group, an aryl group or an aralkyl group; $R^2$ represents an alkyl group, an aryl group, an aralkyl group, a halogen atom or a group of $R^1NH$; Z represents an atomic group necessary to form a carbon ring condensed to the benzene ring; n represents 0, 1 or 2; m represents 0 or an integer from 1 to 7 and m+n is not more than 7; l represents 0 or 1; and each of $R^1$ and $R^2$ may be the same or different when m or n represents 2 or more, respectively.

In accordance with the method of the present invention, a clear color image having a high density can be obtained by a simple procedure and the light-sensitive material has an improved stability during preservation before heat-development procedure and the occurrence of fog and the change in the maximum density are restrained.

A light-sensitive material comprising a support having thereon at least a light sensitive silver halide, a binder, a dye releasing redox compound which is capable of reducing the light sensitive silver halide and is capable of reacting with the light-sensitive silver halide by heating to release a hydrophilic dye and a compound represented by the general formula (A) above is also disclosed.

25 Claims, No Drawings

HEAT DEVELOPABLE ELEMENT WITH STABILIZER

FIELD OF THE INVENTION

The present invention relates to a novel method of forming a dye image by heating under the condition substantially free from water. The present invention also relates to a novel light-sensitive material containing a dye releasing redox compound capable of reacting with a light-sensitive silver halide by heating under the condition substantially free from water to release a hydrophilic dye. Particularly, the present invention relates to a novel method of forming a dye image by transferring a dye released upon heating to a dye fixing layer.

BACKGROUND OF THE INVENTION

Photographic processes using silver halide have been most widely used in the past due to their excellent photographic properties such as sensitivity or control of gradation, etc., as compared with other photographic processes, such as an electrophotographic process or a diazo photographic process. In recent years, with respect to image formation processes for light-sensitive materials using silver halide, many techniques capable of easily and quickly obtaining images have been developed by changing the conventional wet process using a developing solution into a dry development process such as a process using heat, etc.

Heat-developable light-sensitive materials are known in the field of these techniques. Heat-developable light-sensitive materials and processes therefor have been described, for example, in *Shashin Kogaku no Kiso* (*The Foundation of Photographic Technology*), pages 553 to 555 (published by Corona Co., 1979), *Eizo Jyoho* (*The Image Information*), page 40 (April, 1978), *Nebletts Handbook of Photography and Reprography*, 7th Ed., pages 32 to 33 (Van Nostrand Reinhold Company), U.S. Pat. Nos. 3,152,904, 3,301,678, 3,392,020 and 3,457,075, British Pat. Nos. 1,131,108 and 1,167,777, and *Research Disclosure*, No. 17029, pages 9 to 15 (June, 1978).

Many different processes for obtaining color images by dry processes have been proposed. With respect to processes for forming color images by the reaction of an oxidation product of a developing agent with a coupler, it has been proposed to use a p-phenylenediamine type reducing agent and a phenolic coupler or an active methylene coupler as described in U.S. Pat. No. 3,531,286, a p-aminophenol type reducing agent as described in U.S. Pat. No. 3,761,270, a sulfonamidophenol type reducing agent as described in Belgian Pat. No. 802,519 and *Research Disclosure*, pages 31 and 32 (Sept., 1975) and the combination of a sulfonamidophenol type reducing agent and a 4-equivalent coupler as described in U.S. Pat. No. 4,021,240. These processes, however, are disadvantageous in that turbid color images are formed, because a reduced silver image and a color image are simultaneously formed on the exposed area after heat-development. In order to eliminate these disadvantages, there have been proposed a process which comprises removing a silver image by liquid processing or a process which comprises transferring only the dye to another layer, for example, a sheet having an image receiving layer. However, the latter process is not desirable because it is not easy to transfer only the dye as distinguishable from unreacted substances.

Another process which comprises introducing a nitrogen containing heterocyclic group into a dye, forming a silver salt and releasing a dye by heat-development has been described in *Research Disclosure*, No. 16966, pages 54 to 58 (May, 1978). According to this process, clear images cannot be obtained, because it is difficult to control the release of dyes from nonexposed areas, and thus it is not a conventionally applicable process.

Also, processes for forming a positive color image by a heat-sensitive silver dye bleach process, with useful dyes and methods for bleaching have been described, for example, in *Research Disclosure*, No. 14433, pages 30 to 32 (April, 1976), ibid., No. 15227, pages 14 and 15 (December, 1976) and U.S. Pat. No. 4,235,957, etc.

However, this process requires an additional step and an additional material for accelerating bleaching of dyes, for example, heating with a superposed sheet with an activating agent. Furthermore, it is not desirable because the resulting color images are gradually reduced and bleached by coexisting free silver during long periods of preservation.

Moreover, a process for forming a color image utilizing a leuco dye has been described, for example, in U.S. Pat. Nos. 3,985,565 and 4,022,617. However, this process is not desirable because it is difficult to stably incorporate the leuco dye in the photographic material and coloration gradually occurs during preservation.

SUMMARY OF THE INVENTION

The present invention provides a novle method for forming a dye image by heating under the condition substantially free from water, eliminating the drawbacks present in known materials.

Therefore an object of the present invention is to provide a novel method for forming an image which comprises transferring a mobile hydrophilic dye released by heating under the condition substantially free from water into a dye fixing layer to obtain a dye image.

Another object of the present invention is to provide a method for improving stability of the light-sensitive material with the passage of time. The term "stability with the passage of time" used herein means stability during preservation of the light-sensitive material before heat-development procedure. More specifically, the improvement in stability with the passage of time means the occurrence of fog and the change in the maximum density during preservation of the light-sensitive material before heat-development procedure are restrained.

Still another object of the present invention is to provide a method for obtaining a clear dye image by a simple procedure.

These and other objects of the present invention will become more apparent from the following detailed description and examples.

These objects of the present invention are accomplished with a method of forming an image comprising heating a light-sensitive material having at least a light-sensitive silver halide, a binder and a dye releasing redox compound which is capable of reducing the light-sensitive silver halide and is capable of reacting with the light-sensitive silver halide by heating to release a hydrophilic dye on a support under the condition substantially free from water after or simultaneously with imagewise exposure in the presence of a compound represented by the general formula (A) described below to form imagewise a mobile dye.

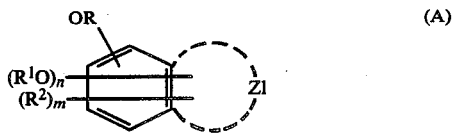

wherein R represents an alkyl group, a cycloalkyl group, an aryl group or an aralkyl group; $R^1$ represents an alkyl group, a cycloalkyl group, an aryl group or an aralkyl group; $R^2$ represents an alkyl group, an aryl group, an aralkyl group, a halogen atom or a group of $R^1NH$; Z represents an atomic group necessary to form a carbon ring condensed to the benzene ring; n represents 0, 1 or 2; m represents 0 or an integer from 1 to 7 and m+n is not more than 7, l represents 0 or 1; and each of $R^1$ and $R^2$ may be the same or different when m or n represents 2 or more, respectively.

DETAILED DESCRIPTION OF THE INVENTION

In the general formula (A), the substituents $R^1O$— and $R^2$— may be present at any position of the benzene ring or the condensed ring of the benzene ring with the carbon ring of Z, that is, naphthalene ring.

Preferred embodiment for R in the general formula (A) is an alkyl group having from 1 to 20 carbon atoms (more preferably from 1 to 10 carbon atoms), for example, a methyl group, an ethyl group, a propyl group, an isopropyl group, a butyl group, a sec-butyl group, an isobutyl group, a tert-butyl group, a pentyl group, a tert-pentyl group, a hexyl group, a heptyl group, an octyl group, a nonyl group, a decyl group, an undecyl group, a dodecyl group, a tridecyl group, a pentadecyl group, a hexadecyl group, a heptadecyl group, an octadecyl group, etc. The alkyl group is generally represented by the formula of $C_kH_{2k+1}$— wherein k is an integer from 1 to 40, more preferably from 1 to 20.

The alkyl group represented by R may be substituted with an alkoxy group having from 1 to 20 carbon atoms (preferably from 1 to 10 carbon atoms) or a substituted alkoxy group, for example, a methoxy group, an ethoxy group, a butoxy group, a group represented by the formula of $ArO(CH_2CH_2O-)_z$ wherein z represents an integer from 1 to 5; and Ar represents an aryl group as defined for R, etc.

Another preferred embodiment for R is a cycloalkyl group having from 3 to 20 carbon atoms (more preferably from 5 to 10 carbon atoms). It is preferably represented by the general formula of $C_kH_{2k-p}$— wherein k represents an integer from 3 to 20 carbon atoms, more preferably from 3 to 10 carbon atoms; and p represents 1, 3, 5 or 7. Examples of the cycloalkyl group include a cyclopentyl group, a cyclohexyl group, a cycloheptyl group, a cyclododecyl group, a cyclohexenyl group, an adamantyl group, etc.

Still another preferred embodiment for R is an aryl group having from 6 to 30 carbon atoms (more preferably from 6 to 20 carbon atoms) including a phenyl group, a substituted phenyl group, a naphthyl group and a substituted naphthyl group. Examples of the substituent include an alkyl group, an alkoxy group, an alkylamino group, an arylamino group, an acyloxy group, an aryloxy group, etc., provided that the total number of carbon atoms included is within the range as described above.

Still another preferred embodiment for R is an aralkyl group having from 7 to 30 carbon atoms (more preferably from 7 to 20 carbon atoms). The aryl moiety of the aralkyl group may be substituted with an alkyl group, an alkoxy group, an alkylamino group, an arylamino group or an acyloxy group, provided that the total number of carbon atoms included is within the range as described above. Examples of the aralkyl group include a benzyl group, a p-methoxybenzyl group, a 2-phenylethyl group, a 2-(p-methoxyphenyl)ethyl group, etc.

Preferred embodiment for $R^1$ in the general formula (A) is an alkyl group having from 1 to 20 carbon atoms (more preferably from 1 to 10 carbon atoms), for example, a methyl group, an ethyl group, a propyl group, an isopropyl group, a butyl group, a sec-butyl group, an isobutyl group, a tert-butyl group, a pentyl group, a tert-pentyl group, a hexyl group, a heptyl group, an octyl group, a nonyl group, a decyl group, an undecyl group, a dodecyl group, a tridecyl group, a pentadecyl group, a hexadecyl group, a heptadecyl group, an octadecyl group, etc. The alkyl group is generally represented by the formula of $C_kH_{2k+1}$— wherein k is an integer from 1 to 40, more preferably from 1 to 20.

The alkyl group represented by $R^1$ may be substituted with an alkoxy group having from 1 to 20 carbon atoms (preferably from 1 to 10 carbon atoms) or a substituted alkoxy group, for example, a methoxy group, an ethoxy group, a butoxy group, a group represented by the formula of $ArO(CH_2CH_2O-)_z$ wherein z represents an integer from 1 to 5; and Ar represents an aryl group as defined for R, etc.

Another preferred embodiment for $R^1$ is a cycloalkyl group having from 3 to 20 carbon atoms (more preferably from 5 to 10 carbon atoms). The cycloalkyl group is preferably represented by the general formula of $C_kH_{2k-p}$— wherein k represents an integer from 3 to 20 carbon atoms, more preferably from 5 to 10 carbon atoms; and p represents 1, 3, 5 or 7. Examples of the cycloalkyl group include a cyclopentyl group, a cyclohexyl group, a cycloheptyl group, a cyclododecyl group, a cyclohexenyl group, an adamantyl group, etc.

Still another preferred embodiment for $R^1$ is an aryl group having from 6 to 30 carbon atoms (more preferably from 6 to 20 carbon atoms) including a phenyl group, a substituted phenyl group, a naphthyl group and a substituted naphthyl group. Examples of the substituent include an alkyl group, an alkoxy group, an alkylamino group, an arylamino group, an acyloxy group, an aryloxy group, etc., provided that the total number of the carbon atoms included is within the range as described above.

Still another preferred embodiment for $R^1$ is an aralkyl group having from 7 to 30 carbon atoms (more preferably from 7 to 20 carbon atoms). The aryl moiety of the aralkyl group may be substituted with an alkyl group, an alkoxy group, an alkylamino group, an arylamino group or an acyloxy group, provided that the total number of the carbon atoms included is within the range as described above. Examples of the aralkyl group include a benzyl group, a p-methoxybenzyl group, a 2-phenylethyl group, a 2-(p-methoxyphenyl)ethyl group, etc.

Preferred embodiment for $R^2$ in the general formula (A) is an alkyl group having from 1 to 20 carbon atoms (more preferably from 1 to 10 carbon atoms), for example, a methyl group, an ethyl group, a propyl group, an isopropyl group, a butyl group, a sec-butyl group, an isobutyl group, a tert-butyl group, a pentyl group, a tert-pentyl group, a hexyl group, a heptyl group, an octyl group, a nonyl group, a decyl group, an undecyl group, a dodecyl group, a tridecyl group, a pentadecyl group, a hexadecyl group, a heptadecyl group, an octadecyl group, etc. It is generally represented by the formula of $C_kH_{2k+1}$— wherein k is an integer from 1 to 20, more preferably from 1 to 10, The alkyl group represented by $R^2$ may be substituted with an alkoxy group having from 1 to 20 carbon atoms (preferably from 1 to 10 carbon atoms) or a substituted alkoxy group, for example, a methoxy group, an ethoxy group, a butoxy group, a group represented by the formula of $ArO(CH_2CH_2O-)_z$ wherein z represents an integer from 1 to 5; and Ar represents an aryl group as defined for R, etc.

Another preferred embodiment for $R^2$ is an aryl group having from 6 to 30 carbon atoms (more preferably from 6 to 20 carbon atoms) including a phenyl group, a substituted phenyl group, a naphthyl group and a substituted naphthyl group. Examples of the substituent include an alkyl group, an alkoxy group, an alkylamino group, an arylamino group, an acyloxy group, etc., provided that the total number of the carbon atoms included is within the range as described above.

Still another preferred embodiment for $R^2$ is an aralkyl group having from 7 to 30 carbon atoms (more preferably from 7 to 20 carbon atoms). The aryl moiety of the aralkyl group may be substituted with an alkyl group, an alkoxy group, an alkylamino group, an arylamino group or an acyloxy group, provided that the total number of the carbon atoms included is within the range as described above. Examples of the aralkyl group include a benzyl group, a p-methoxybenzyl group, a 2-phenylethyl group, a 2-(p-methoxyphenyl)ethyl group, etc., a 2-(p-ethoxyphenyl)propyl group, etc.

When l in the general formula (A) is 1, Z preferably represents an atomic group necessary to form a benzene ring. In this case it is understood that a naphthalene ring is formed in the general formula (A).

m in the general formula (A) is preferably 0, 1 or 2, and n in the general formula (A) is preferably 0 or 1.

Specific examples of the compound represented by the general formula (A) in the present invention are set forth below, but the present invention should not be construed as being limited thereto.

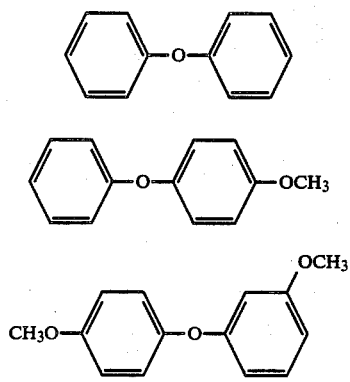

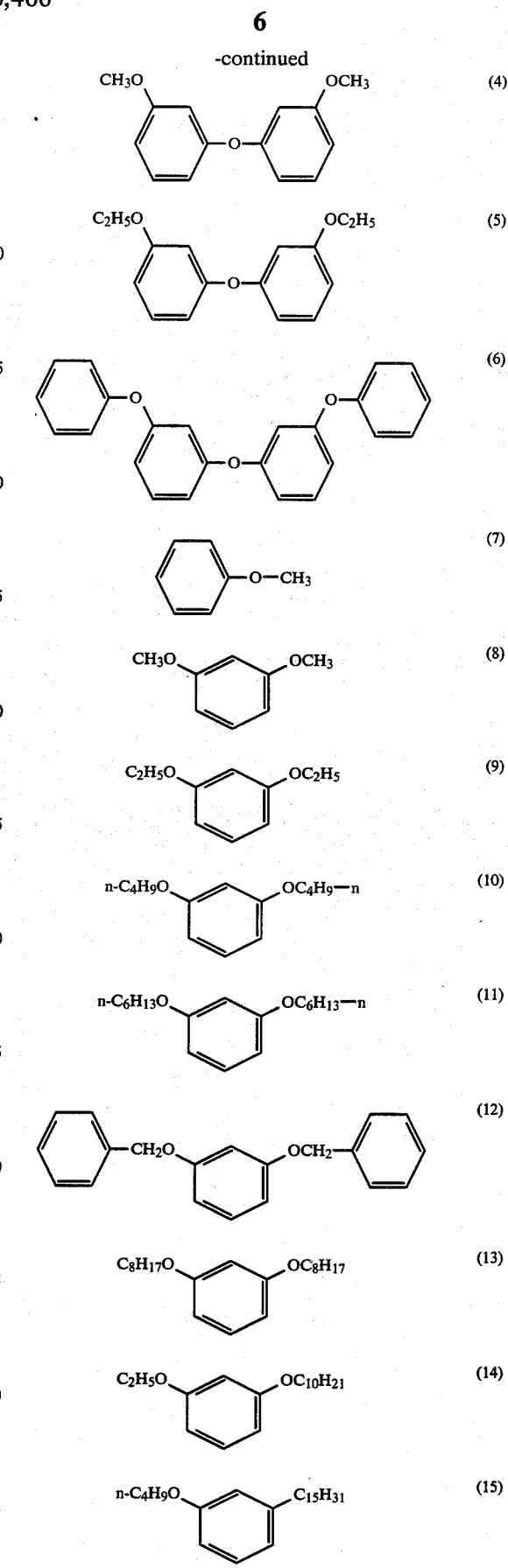

-continued

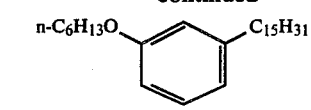  (16)

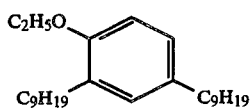  (17)

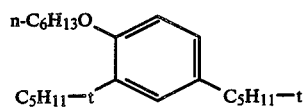  (18)

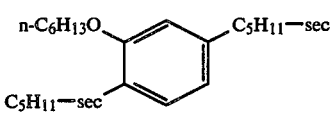  (19)

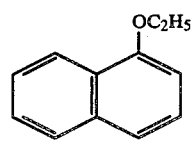  (20)

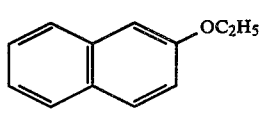  (21)

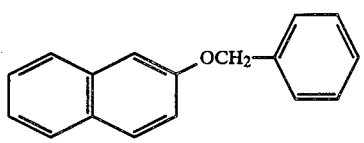  (22)

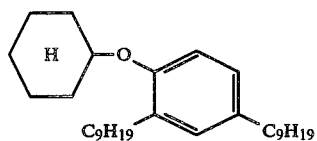  (23)

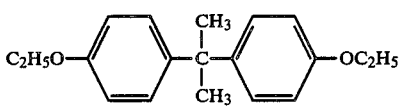  (24)

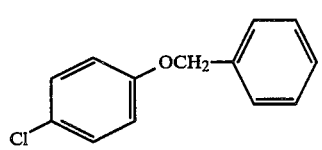  (25)

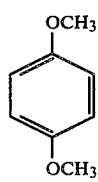  (26)

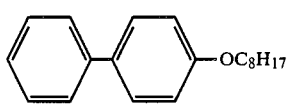  (27)

-continued

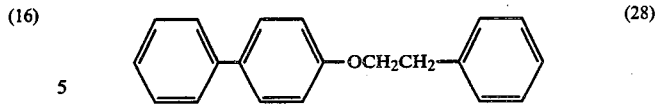  (28)

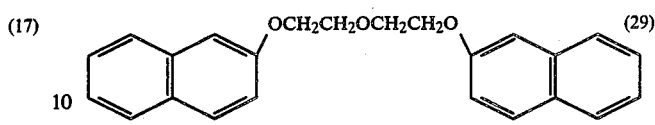  (29)

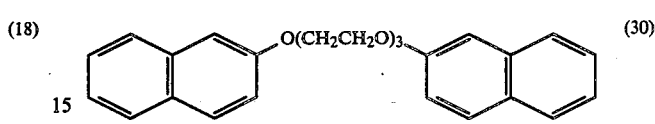  (30)

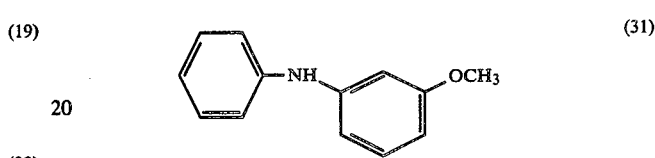  (31)

  (32)

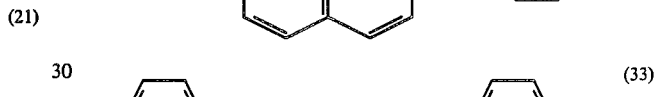  (33)

The compound represented by the general formula (A) can be generally synthesized by the so-called Williamson. Synthesis wherein a compound having a hydroxy group, i.e., a phenol or an alcohol is reacted with an alkylating agent such as a halide. Alternatively, the compound represented by the general formula (A) can be synthesized by dehydration condensation of two kinds of phenols and/or alcohols. These various methods are described in detail in S. R. Sandler and W. Karo, *Organic Functional Group Preparation*, pages 99 to 115 (Academic Press, 1968).

Specific example of synthesizing 2-ethoxynaphthalene is set forth in the following.

SYNTHESIS EXAMPLE

Synthesis of 2-Ethoxynaphthalene 450 g of β-naphthol, 200 ml of ethanol and 50 ml of 98% sulfuric acid were mixed and after finishing the generation of heat the mixture was heated on a steam bath for 4 hours. After allowing to stand and cool, the lower layer was removed. Then the procedures wherein to the residue were added 40 ml of ethanol and 20 ml of 98% sulfuric acid, the mixture was heated on a steam bath for 3 hours and the lower layer was removed after allowing to stand and cool were repeated three times. The organic layer was washed with water to which was added an aqueous solution of sodium hydroxide (40 g of sodium hydroxide dissolved in 1 liter of water) and the mixture was warmed and shaked. While it was warm, the lower layer was removed, the upper layer was poured into an aqueous solution of sodium hydroxide and cooled to solidified. The solid was collected by filtration, washed with water and air-dried. Yield: 461 g.

Other compounds may be synthesized in the same manner as or with reference to the above-described synthesis example.

The compounds according to the present invention are dispersed in an aqueous solution of a hydrophilic colloid using a dispersing aid, individually or as a mixture of two or more thereof. Suitable examples of the dispersion methods are described in U.S. Pat. Nos. 2,304,939, 2,322,027, 2,801,170, 2,801,171 and 2,949,360, etc. In these cases, the compounds according to the present invention may be used together with an organic solvent having a high boiling point, for example, a phthalic acid alkyl ester (for example, dibutyl phthalate, dioctyl phthalate, etc.), a phosphoric acid ester (for example, diphenyl phosphate, triphenyl phosphate, tricresyl phosphate, dioctylbutyl phosphate, etc.), a citric acid ester (for example, tributyl acetylcitrate, etc.), a benzoic acid ester (for example, octyl benzoate, etc.), an alkylamide (for example, diethyl laurylamide, etc.), an aliphatic acid ester (for example, dibutoxyethyl succinate, dioctyl azelate, etc.), a trimesic acid ester (for example, tributyl trimesate, etc.), etc.

Usually, the compounds according to the present invention are dispersed in an aqueous solution of a hydrophilic colloid using a dispersing aid together with the dye releasing redox compound and an organic solvent having a low boiling point of about 30° C. to 160° C. If desired, other photographic additives can be dispersed at the same time. Useful examples of the organic solvent having a boiling point of about 30° C. to 160° C. include a lower alkyl acetate such as ethyl acetate, butyl acetate, etc., ethyl propionate, secondary butyl alcohol, methyl isobutyl ketone, $\beta$-ethoxyethyl acetate, methyl cellosolve acetate, cyclohexanone, etc.

Also, as the dispersing aid, an anionic surface active agent (for example, sodium alkylbenzenesulfonate, sodium dioctylsulfosuccinate, sodium dodecylsulfate, sodium alkylnaphthalenesulfonate, a Fischer type coupler, etc.), an amphoteric surface active agent (for example, N-tetradecyl-N,N-dipolyethylene-$\alpha$-betaine, etc.) and a nonionic surface active agent (for example, sorbitan monolaurate, etc.) are usually employed. Further, the surface active agent described in other part of the specification may also be used as the dispersion aid.

The dispersion of the compound according to the present invention containing the dye releasing redox compound can be added either to one of an emulsion laydr such as a silver halide emulsion layer and an intermediate layer or to both thereof in the heat-developable light-sensitive material. Further, the dispersion of the compound according to the present invention without the dye releasing redox compound can be used in a hydrophilic colloid layer (for example, a surface protective layer, an intermediate layer, etc.) or an emulsion layer (for example, a silver halide emulsion layer, etc.) of the heat-developable light-sensitive material or in a layer containing a mordant or other layers of a dye fixing material as described hereinafter. In order to introduce the compound according to the present invention into a layer of the light-sensitive material, known methods such as a method as described in U.S. Pat. No. 2,322,027 can be used.

The compound according to the present invention can be used usually in a range of 0.01 time to 20 times by weight based on the dye releasing redox compound, and more preferably in a range of 0.01 time to 5 times by weight. Also, when the compound according to the present invention does not contain the dye releasing redox compound, the compound according to the present invention can be preferably used in a range of 0.001 g/m$^2$ to 5 g/m$^2$.

The term "dye image" in the present invention means a multicolor or monocolor dye image. The monocolor dye image includes a monocolor dye image composed of a mixture of two or more dyes.

The method of forming an image according to the present invention can simultaneously provide a silver image and a mobile dye on the part corresponding to the silver image by only heating after imagewise exposure to light. That is, in the color image forming method of the present invention, when the heat-developable color light-sensitive material is imagewise exposed to light and developed by heating under the condition substantially free from water, an oxidation-reduction reaction occurs between a light-sensitive silver halide and a reducing dye releasing redox compound by means of exposed light-sensitive silver halide as a catalyst to form a silver image in the exposed area. In this step, the dye releasing redox compound is oxidized by the silver halide to form an oxidized compound and consequently the hydrophilic mobile dye is released. Accordingly, the silver image and the mobile dye are formed in the exposed area. The above-described reaction is accelerated when a dye releasing activator is present. The mobile dye thus formed is transferred to, for example, a dye fixing layer whereby a dye image is obtained. The above-described process illustrates a case wherein a negative type silver halide emulsion is used. In a case wherein an autopositive type silver halide emulsion is used, the process is the same as the case of using the negative type silver halide emulsion except that a silver image and a mobile dye are formed in the unexposed area.

The oxidation-reduction reaction between a light-sensitive silver halide and a dye releasing redox compound and the dye releasing reaction subsequently occurred are characterized by proceeding under the dry condition substantially free from water at high temperature. The high temperature condition used herein means a temperature condition of 80° C. or higher. The dry condition substantially free from water means a condition which is equilibrium with moisture in the air and to which water is not supplied from the outside of the system. Such a condition is described in *The Theory of the Photographic Process*, 4th Ed., page 374 (edited by T. H. James, Macmillan Co.). It is confirmed from the fact in which a reaction rate of a sample subjected to vacuum drying under a pressure of 10$^{-3}$ mmHg for one day does not decrease that a sufficiently large reaction rate is exhibited under the dry condition substantially free from water.

The dye releasing reaction has been believed to be a reaction by means of the attack with the so-called nucleophilic reagent and is usually carried out in a liquid having a high pH value of 10 or higher. In the present invention, however, the high reaction rate can be achieved under the dry condition of high temperature and substantially free from water which is an unexpected result.

Further, the dye releasing redox compound according to the present invention can undergo an oxidation-reduction reaction with silver halide without the assistance of the so-called auxiliary developing agent. This is also an unexpected result based on previous information of what may happen at ambient temperature in a wet type of development.

The above-described reaction is particularly accelerated in the presence of an organic silver salt oxidizing agent to provide a high image density. Therefore, it is a particularly preferred embodiment in which the organic silver salt oxidizing agent is coexistent.

The dye releasing redox compound which releases a hydrophilic diffusible dye used in the present invention is a compound described in European Patent Application (OPI) No. 76,492 as a dye releasing compound and is represented by the following general formula:

wherein $R_a$ represents a reducing group capable of being oxidized by the silver halide; and D represents an image forming dye portion containing a hydrophilic group.

The above-described compound is oxidized correspondingly to or reversely corresponding to latent image distributed imagewise in the silver halide and releases imagewise a mobile dye.

The detail definitions of $R_a$ and D, examples of the specific compounds and synthesis examples thereof are described in European Patent Application (OPI) No. 76,492.

As the dye releasing redox compounds used in the present invention, the compounds described, for example, in U.S. Pat. No. 4,055,428, Japanese Patent Application (OPI) Nos. 12642/81, 16130/81, 16131/81, 650/82 and 4043/82, U.S. Pat. Nos. 3,928,312 and 4,076,529, U.S. Published Patent Application No. B 351,673, U.S. Pat. Nos. 4,135,929 and 4,198,235, Japanese Patent Application (OPI) No. 46730/78, U.S. Pat. Nos. 4,273,855, 4,149,892, 4,142,891 and 4,258,120, etc., are also effective in addition to the above-described compounds.

Further, the dye releasing redox compounds which release a yellow dye as described, for example, in U.S. Pat. Nos. 4,013,633, 4,156,609, 4,148,641, 4,165,987, 4,148,643, 4,183,755, 4,246,414, 4,268,625 and 4,245,028, Japanese Patent Application (OPI) Nos. 71072/81, 25737/81, 138744/80, 134849/80, 106727/77, 114930/76, etc., can be effectively used in the present invention.

The dye releasing redox compounds which release a magenta dye as described, for example, in U.S. Pat. Nos. 3,954,476, 3,932,380, 3,931,144, 3,932,381, 4,268,624 and 4,255,509, Japanese Patent Application (OPI) Nos. 73057/81, 71060/81, 134850/80, 40402/80, 36804/80, 23628/78, 106727/77, 33142/80 and 53329/80, etc., can be effectively used in the present invention.

The dye releasing redox compounds which release a cyan dye as described, for example, in U.S. Pat. Nos. 3,929,760, 4,013,635, 3,942,987, 4,273,708, 4,148,642, 4,183,754, 4,147,544, 4,165,238, 4,246,414 and 4,268,625, Japanese Patent Application (OPI) Nos. 71061/81, 47823/78, 8827/77 and 143323/78, etc., can be effectively used in the present invention.

Two or more of the dye releasing redox compounds can be used together. In these cases, two or more dye releasing redox compounds may be used together in order to represent the same color or in order to represent black color.

The dye releasing redox compounds are suitably used in a range from 10 mg/m² to 15 g/m² and preferably in a range from 20 mg/m² to 10 g/m² in a total.

The dye releasing redox compound used in the present invention can be introduced into a layer of the light-sensitive material by known methods such as a method as described in U.S. Pat. Nos. 2,322,027. In this case, an organic solvent having a high boiling point or an organic solvent having a low boiling point as described above can be used.

Further, it is possible to use a dispersion method using a polymer as described in Japanese Patent Publication No. 39853/76 and Japanese Patent Application (OPI) No. 59943/76. Moreover, various surface active agents can be used when the dye releasing redox compound is dispersed in a hydrophilic colloid. For this purpose, the surface active agents illustrated in other part of the specification can be used.

In the present invention, if necessary, a reducing agent may be used. The reducing agent in this case is the so-called auxiliary developing agent, which is oxidized by the silver halide and/or the organic silver salt oxidizing agent to form its oxidized product having an ability to oxidize the reducing group $R_a$ in the dye releasing redox compound.

Examples of useful auxiliary developing agents include the compounds specifically described in European Patent Application (OPI) No. 76,492.

In the present invention, an amount of the reducing agent added is from 0.0005 mol to 20 mols per mol of silver and more preferably from 0.001 mol to 4 mols per mol of silver.

The silver halide used in the present invention includes silver chloride, silver chlorobromide, silver chloroiodide, silver bromide, silver iodobromide, silver chloroiodobromide and silver iodide, etc.

In the embodiment of the present invention in which the organic silver salt oxidizing agent is not used together with but the silver halide is used alone, particularly preferred silver halide is silver halide partially containing a silver iodide crystal in its grain. That is, the silver halide which shows the X-ray diffraction pattern of pure silver iodide is particularly preferred.

In photographic materials a silver halide containing two or more kinds of halogen atoms can be used. Such a silver halide is present in the form of a completely mixed crystal in a conventional silver halide emulsion. For example, the grain of silver iodobromide shows X-ray diffraction pattern at a position corresponding to the mixed ratio of silver iodide crystal and silver bromide crystal but not at a position corresponding to pure silver iodide crystal and pure silver bromide crystal separately.

Particularly preferred examples of silver halide used in the present invention include silver chloroiodide, silver iodobromide, and silver chloroiodobromide each containing silver iodide crystal in its grain and showing X-ray diffraction pattern of silver iodide crystal.

The process for preparing those silver halides is explained taking the case of silver iodobromide. That is, the silver iodobromide is prepared by first adding silver nitrate solution to potassium bromide solution to form silver bromide particles and then adding potassium iodide to the mixture.

Two or more kinds of silver halides in which a particle size and/or a halogen composition are different from each other may be used in mixture.

An average particle size of the silver halide used in the present invention is preferably from 0.001 μm to 10 μm and more preferably from 0.001 μm to 5 μm.

The silver halide used in the present invention may be used as is. However, it may be chemically sensitized with a chemical sensitizing agent such as compounds or sulfur, selenium or tellurium, etc., or compounds of gold, platinum, palladium, rhodium or iridium, etc., a reducing agent such as tin halide, etc., or a combination thereof. The details thereof are described in T. H. James, *The Theory of the Photographic Process*, the Fourth Edition, Chapter 5, pages 149 to 169.

In the particularly preferred embodiment of the present invention, an organic silver salt oxidizing agent is used together. The organic silver salt oxidizing agent is a silver salt which forms a silver image by reacting with the above-described image forming substance or a reducing agent coexisting, if necessary, with the image forming substance, when it is heated to a temperature of above 80° C. and, preferably, above 100° C. in the presence of exposed silver halide. By coexisting the organic silver salt oxidizing agent, the light-sensitive material which provides higher color density can be obtained.

The silver halide used in this case is not always necessarily to have the characteristic in that the silver halide contains pure silver iodide crystal in the case of using the silver halide alone. Any silver halide which is known in the art can be used.

Examples of such organic silver salt oxidizing agents include those described in European patent application (OPI) No. 76,492.

A silver salt of an organic compound having a carboxy group can be used. Typical examples thereof include a silver salt of an aliphatic carboxylic acid and a silver salt of an aromatic carboxylic acid.

In addition, a silver salt of a compound containing a mercapto group or a thione group and a derivative thereof can be used.

Further, a silver salt of a compound containing an imino group can be used. Examples of these compounds include a silver salt of benzotriazole and a derivative thereof as described in Japanese Patent Publication Nos. 30270/69 and 18416/70, for example, a silver salt of benzotriazole, a silver salt of alkyl substituted benzotriazole such as a silver salt of methylbenzotriazole, etc., a silver salt of a halogen substituted benzotriazole such as a silver salt of 5-chlorobenzotriazole, etc., a silver salt of carboimidobenzotriazole such as a silver salt of butylcarboimidobenzotriazole, etc., a silver salt of 1,2,4-triazole or 1-H-tetrazole as described in U.S. Pat. No. 4,220,709, a silver salt of carbazole, a silver salt of saccharin, a silver salt of imidazole and an imidazole derivative, and the like.

Moreover, a silver salt as described in *Research Disclosure*, Vol. 170, No. 17029 (June, 1978) and an organic metal salt such as copper stearate, etc., are the organic metal salt oxidizing agent capable of being used in the present invention.

Methods of preparing these silver halide and organic silver salt oxidizing agents and manners of blending them are described in *Research Disclosure*, No. 17029, Japanese Patent Application (OPI) Nos. 32928/75 and 42529/76, U.S. Pat. No. 3,700,453, and Japanese Patent Application (OPI) Nos. 13224/74 and 17216/75.

A suitable coating amount of the light-sensitive silver halide and the organic silver salt oxidizing agent employed in the present invention is in a total of from 50 mg/m$^2$ to 10 g/m$^2$ calculated as an amount of silver.

The light-sensitive silver halide and the organic silver salt oxidizing agent used in the present invention are prepared in the binder as described below. Further, the dye releasing redox compound is dispersed in the binder described below.

The binder which can be used in the present invention can be employed individually or in a combination thereof. A hydrophilic binder can be used as the binder according to the present invention. The typical hydrophilic binder is a transparent or translucent hydrophilic colloid, examples of which include a natural substance, for example, protein such as gelatin, a gelatin derivative, etc., a cellulose derivative, a polysaccharide such as starch, gum arabic, etc., and a synthetic polymer, for example, a water-soluble polyvinyl compound such as polyvinyl alcohol, polyvinyl pyrrolidone, acrylamide polymer, etc. Another example of the synthetic polymer compound is a dispersed vinyl compound in a latex form which is used for the purpose of increasing dimensional stability of a photographic material.

The silver halide used in the present invention can be spectrally sensitized with methine dyes or other dyes. Suitable dyes which can be employed include cyanine dyes, merocyanine dyes, complex cyanine dyes, complex merocyanine dyes, holopolar cyanine dyes, hemicyanine dyes, styryl dyes, and hemioxonol dyes. Of these dyes, cyanine dyes, merocyanine dyes and complex merocyanine dyes are particularly useful. Any conventionally utilized nucleus for cyanine dyes, such as basic heterocyclic nuclei, can be contained in these dyes. That is, a pyrroline nucleus, an oxazoline nucleus, a thiazoline nucleus, a pyrrole nucleus, an oxazole nucleus, a thiazole nucleus, a selenazole nucleus, an imidazole nucleus, a tetrazole nucleus, a pyridine nucleus, etc., and further, nuclei formed by condensing alicyclic hydrocarbon rings with these nuclei and nuclei formed by condensing aromatic hydrocarbon rings with these nuclei, that is, an indolenine nucleus, a benzindolenine nucleus, an indole nucleus, a benzoxazole nucleus, a naphthoxazole nucleus, a benzothiazole nucleus, a naphthothiazole nucleus, a benzoselenazole nucleus, a benzimidazole nucleus, a quinoline nucleus, etc., are appropriate. The carbon atoms of these nuclei may also be substituted.

As nuclei having a ketomethylene structure, 5- or 6-membered heterocyclic nuclei such as a pyrazolin-5-one nucleus, a thiohydantoin nucleus, a 2-thiooxazolidin-2,4-dione nucleus, a thiazolidin-2,4-dione nucleus, a rhodanine nucleus, a thiobarbituric acid nucleus, etc., may also be used in merocyanine dyes and complex merocyanine dyes.

These sensitizing dyes can be employed individually, and can also be employed in combination thereof. A combination of sensitizing dyes is often used, particularly for the purpose of supersensitization. Representative examples thereof are described in U.S. Pat. Nos. 2,688,545, 2,977,229, 3,397,060, 3,522,052, 3,527,641, 3,617,293, 3,628,964, 3,666,480, 3,672,898, 3,679,428, 3,703,377, 3,769,301, 3,814,609, 3,837,862 and 4,026,707, British Pat. Nos. 1,344,281 and 1,507,803, Japanese Patent Publication Nos. 4936/68 and 12375/78, Japanese Patent Application (OPI) Nos. 110618/77 and 109925/77, etc.

The sensitizing dyes may be present in the emulsion together with dyes which themselves do not give rise to spectrally sensitizing effects but exhibit a supersensitizing effect or materials which do not substantially absorb visible light but exhibit a supersensitizing effect. For example, aminostilbene compounds substituted with a nitrogen-containing heterocyclic group (e.g., those described in U.S. Pat. Nos. 2,933,390 and 3,635,721), aromatic organic acid-formaldehyde condensates (e.g., those described in U.S. Pat. No. 3,743,510), cadmium salts, azaindene compounds, etc., can be present. The combinations described in U.S. Pat. Nos. 3,615,613, 3,615,641, 3,617,295 and 3,635,721 are particularly useful.

A support used in the light-sensitive material or used as the dye fixing material, if desired, according to the present invention is that which can endure at the processing temperature. As an ordinary support, not only glass, paper, metal or analogues thereto may be used, but also an acetyl cellulose film, a cellulose ester film, a polyvinyl acetal film, a polystyrene film, a polycarbonate film, a polyethylene terephthalate film, and a film related thereto or a plastic material may be used. Further, a paper support laminated with a polymer such as polyethylene, etc., can be used. The polyesters described in U.S. Pat. Nos. 3,634,089 and 3,725,070 are preferably used.

In the present invention, various kinds of dye releasing activators can be used. The dye releasing activator means a substance which accelerates the oxidation-reduction reaction between the light-sensitive silver halide and/or the organic silver salt oxidizing agent and dye releasing redox compound, or accelerates release of a dye by means of its nucleophilic action to the oxidized dye releasing redox compound in the dye releasing reaction subsequently occurred, and a base and a base precursor can be used. It is particularly advantageous to use these dye releasing activators in order to accelerate the reactions in the present invention.

Examples of preferred bases are amines which include trialkylamines, hydroxylamines, aliphatic polyamines, N-alkyl substituted aromatic amines, N-hydroxyalkyl substituted aromatic amines and bis[p-(dialkylamino)phenyl]methanes. Further, betaine tetramethylammonium iodide and diaminobutane dihydrochloride as described in U.S. Pat. No. 2,410,644, and urea and organic compounds including amino acids such as 6-aminocaproic acid as described in U.S. Pat. No. 3,506,444 are useful. The base precursor is a substance which releases a basic component by heating. Examples of typical base precursors are described in British Pat. No. 998,949. A preferred base precursor is a salt of a carboxylic acid and an organic base, and examples of the suitable carboxylic acids include trichloroacetic acid and trifluoroacetic acid and examples of the suitable bases include guanidine, piperidine, morpholine, p-toluidine and 2-picoline, etc. Guanidine trichloroacetate as described in U.S. Pat. No. 3,220,846 is particularly preferred. Further, aldonic amides as described in Japanese Patent Application (OPI) No. 22625/75 are preferably used because they decompose at a high temperature to form bases.

These dye releasing activators can be used in an amount of a broad range. A useful range is up to 50% by weight based on the amount of a dry layer coated of the light-sensitive material. A range of 0.01% by weight to 40% by weight is more preferred.

It is advantageous to use a compound represented by the general formula described below in the heat-developable color photographic material in order to accelerate development and accelerate release of a dye.

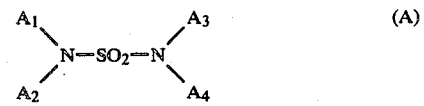

wherein $A_1$, $A_2$, $A_3$ and $A_4$, which may be the same or different, each represents a hydrogen atom or a substituent selected from an alkyl group, a substituted alkyl group, a cycloalkyl group, an aralkyl group, an aryl group, a substituted aryl group and a heterocyclic group; and $A_1$ and $A_2$ or $A_3$ and $A_4$ may combine with each other to form a ring.

The above-described compound can be used in an amount of broad range. A useful range is up to 20% by weight based on the amount of a dry layer coated of the light-sensitive material. A range of 0.1% by weight to 15% by weight is more preferred.

It is advantageous to use a water releasing compound in the present invention in order to accelerate the dye releasing reaction.

The water releasing compound means a compound which releases water by decomposition during heat development. These compounds are particularly known in the field of printing of fabrics, and $NH_4Fe(SO_4)_2 \cdot 12H_2O$, etc., as described in Japanese Patent Application (OPI) No. 88386/75 are useful.

Further, in the present invention, it is possible to use a compound which activates development and stabilizes the image at the same time. Particularly, it is preferred to use isothiuroniums including 2-hydroxyethylisothiuronium trichloroacetate as described in U.S. Pat. No. 3,301,678, bisisothiuroniums including 1,8-(3,6-dioxaoctane)bis(isothiuronium trifluoroacetate), etc., as described in U.S. Pat. No. 3,669,670, thiol compounds as described in German Patent Application (OLS) No. 2,162,714, thiazolium compounds such as 2-amino-2-thiazolium trichloroacetate, 2-amino-5-bromo-ethyl-2-thiazolium trichloroacetate, etc., as described in U.S. Pat. No. 4,012,260, compounds having α-sulfonylacetate as an acid part such as bis(2-amino-2-thiazolium)-methylene-bis(sulfonylacetate), 2-amino-2-thiazolium phenylsulfonylacetate, etc., as described in U.S. Pat. No. 4,060,420, and compounds having 2-carboxycarboxamide as an acid part as described in U.S. Pat. No. 4,088,496.

In the present invention, it is possible to use a thermal solvent. The term "thermal solvent" means a non-hydrolyzable organic material which melts at a temperature of heat treatment and melts at a lower temperature of heat treatment when it is present together with other components. Preferred examples of thermal solvents include compounds which can act as a solvent for the developing agent and compounds having a high dielectric constant which accelerate physical development of silver salts. Examples of preferred thermal solvents include those described in European Patent Application (OPI) No. 76,492.

In the present invention, though it is not always necessary to further incorporate substances or dyes for preventing irradiation or halation in the light-sensitive material, because the light-sensitive material is colored by the dye releasing redox compound, it is possible to add filter dyes or light absorbing materials, etc., into the light-sensitive material, as described in Japanese Patent Publication No. 3692/73 and U.S. Pat. Nos. 3,253,921, 2,527,583 and 2,956,879, etc., in order to further improve sharpness. It is preferred that these dyes have a thermal bleaching property. For example, dyes as described in U.S. Pat. Nos. 3,769,019, 3,745,009 and 3,615,432 are preferred.

The light-sensitive material used in the present invention may contain, if necessary, various additives known for the heat-developable light-sensitive materials and may have a layer other than the light-sensitive layer, for example, an antistatic layer, an electrically conductive layer, a protective layer, an intermediate layer, an antihalation layer, a strippable layer, etc.

The photographic emulsion layer and other hydrophilic colloid layers in the light-sensitive material of the present invention may contain various surface active agents for various purposes, for example, as coating aids, or for prevention of electrically charging, improvement of lubricating property, emulsification, prevention of adhesion, improvement of photographic properties (for example, acceleration of development, rendering hard tone or sensitization), etc.

For example, it is possible to use nonionic surface active agents such as saponin (steroid saponin), alkylene oxide derivatives (for example, polyethylene glycol, polyethylene glycol/polypropylene glycol condensates, polyethylene glycol alkyl ethers or polyethylene glycol alkylaryl ethers, polyethylene glycol esters, polyethylene glycol sorbitan esters, polyalkylene glycol alkylamines or amides, polyethylene oxide adducts of silicone, etc.), glycidol derivatives (for example, alkenylsuccinic acid polyglycerides, alkylphenol polyglycerides, etc.), polyhydric alcohol aliphatic acid esters or saccharide alkyl esters, etc.; anionic surface active agents containing acid groups such as carboxy group, a sulfo group, a phospho group, a sulfate group, a phosphate group, etc., such as alkylcarboxylic acid salts, alkylsulfonate salts, alkylbenzenesulfonate salts, alkylnaphthalenesulfonate salts, alkyl sulfuric acid esters, alkylphosphoric acid esters, N-acyl-N-alkyltaurines, sulfosuccinic acid esters, sulfoalkyl polyoxyethylene alkylphenyl ethers, polyoxyethylene alkylphosphoric acid esters, etc.; ampholytic surface active agents such as amino acids, aminoalkylsulfonic acids, aminoalkylsulfuric acid esters or phosphoric acid esters, alkylbetaines, amine oxides, etc.; and cationic surface active agents such as alkylamine salts, aliphatic or aromatic quaternary ammonium salts, heterocyclic quaternary ammonium salts such as pyridinium salts, imidazolium salts, etc., aliphatic or heterocyclic phosphonium salts, aliphatic or heterocyclic sulfonium salts, etc.

Of the above-described surface active agents, polyethylene glycol type nonionic surface active agents having a recurring unit of ethylene oxide in their molecules may be preferably incorporated into the light-sensitive material. It is particularly preferred that the molecule contains 5 or more of the recurring units of ethylene oxide.

The nonionic surface active agents capable of satisfying the above-described conditions are well known as to their structures, properties and methods of synthesis. These nonionic surface active agents are widely used even outside this field. Representative references relating to these agents include: *Surfactant Science Series,* Vol. 1, *Nonionic Surfactants* (edited by Martin J. Schick, Marcel Dekker Inc., 1967), and *Surface Active Ethylene Oxide Adducts* (edited by Schoufeldt N. Pergamon Press, 1969). Among the nonionic surface active agents described in the above-mentioned references, those capable of satisfying the above-described conditions are preferably employed in connection with the present invention.

The nonionic surface active agents can be used individually or as a mixture of two or more of them.

The polyethylene glycol type nonionic surface active agents can be used in an amount of less than 100% by weight, preferably less than 50% by weight, based on a hydrophilic binder.

The light-sensitive material of the present invention may contain a cationic compound containing a pyridinium salt. Examples of the cationic compounds containing a pyridinium group used are described in PSA Journal Section B 36 (1953), U.S. Pat. Nos. 2,648,604 and 3,671,247, Japanese Patent Publication Nos. 30074/69 and 9503/69, etc.

In the photographic light-sensitive material and the dye fixing material of the present invention, the photographic emulsion layer and other binder layers may contain inorganic or organic hardeners. It is possible to use chromium salts (chromium alum, chromium acetate, etc.), aldehydes (formaldehyde, glyoxal, glutaraldehyde, etc.), N-methylol compounds (dimethylolurea, methylol dimethylhydantoin, etc.), dioxane derivatives (2,3-dihydroxydioxane, etc.), active vinyl compounds (1,3,5-triacryloylhexahydro-s-triazine, 1,3-vinylsulfonyl-2-propanol, etc.), active halogen compounds (2,4-dichloro-6-hydroxy-s-triazine, etc.), mucohalogenic acids (mucochloric acid, mucophenoxychloric acid, etc.), etc., which are used individually or as a combination thereof.

Examples of various additives include those, described in *Research Disclosure,* Vol. 170, No. 17029 (June, 1978), for example, plasticizers, dyes for improving sharpness, antihalation dyes, sensitizing dyes, matting agents, fluorescent whitening agents and fading preventing agents, etc.

If necessary, two or more layers may be coated at the same time by the method as described in U.S. Pat. No. 2,761,791 and British Pat. No. 837,095.

Various means for exposure can be used in the present invention. Latent images are obtained by imagewise exposure by radiant rays including visible rays. Generally, light sources used in this invention include tungsten lamps, mercury lamps, halogen lamps such as iodine lamps, xenon lamps, laser light sources, CRT light sources, fluorescent tubes and light-emitting diodes, etc.

In the present invention, after the heat-developable color photographic material is exposed to light, the resulting latent image can be developed by heating the whole material to a suitably elevated temperature, for example, about 80° C. to about 250° C. for about 0.5 second to about 300 seconds. A higher temperature or lower temperature can be utilized to prolong or shorten the heating time, if it is within the above-described temperature range. Particularly, a temperature range of about 110° C. to about 160° C. is useful.

As the heating means, a simple heat plate, iron, heat roller, heat generator utilizing carbon or titanium white, etc., or analogues thereto may be used.

In the present invention, a specific method for forming a color image by heat development comprises transfer of a hydrophilic mobile dye. For this purpose, the heat-developable color photographic material of the present invention is composed of a support having thereon a light-sensitive layer (I) containing at least silver halide, if necessary, an organic silver salt oxidizing agent, a dye releasing redox compound which is also a reducing agent for the organic silver salt oxidizing agent and a binder, and a dye fixing layer (II) capable of receiving the hydrophilic diffusible dye formed in the light-sensitive layer (I).

The above-described light-sensitive layer (I) and the dye fixing layer (II) may be formed on the same support, or they may be formed on different supports, respectively. The dye fixing layer (II) can be stripped off the light-sensitive layer (I). For example, after the heat-developable color photographic material is exposed imagewise to light, it is developed by heating uniformly and thereafter the dye fixing layer (II) or the light-sensitive layer (I) is peeled apart. Also, when a light-sensitive material having the light-sensitive layer coated on a support and a fixing material having the dye fixing layer (II) coated on a support are separately formed, after the light-sensitive material is exposed imagewise to light and uniformly heated, the mobile dye can be transferred on the dye fixing layer (II) by superposing the fixing material on the light-sensitive layer.

Further, there is a method wherein only the light-sensitive layer (I) is exposed imagewise to light and heated uniformly be superposing the dye fixing layer (II) on the light-sensitive layer (I).

The dye fixing layer (II) can contain, for example, a dye mordant in order to fix the dye. In the present invention, various mordants can be used, and polymer mordants are particularly preferred. In addition to the mordants, the dye fixing layer may contain the bases, base precursors and thermal solvents. In particular, it is particularly preferred to incorporate the bases or base precursors into the dye fixing layer (II) in the cases wherein the light-sensitive layer (I) and the dye fixing layer are formed on different supports.

Preferred polymer mordants used in the present invention can be polymers containing secondary and tertiary amino groups, polymers containing nitrogen-containing heterocyclic moieties, polymers having quaternary cation groups thereof, having a molecular weight of from 5,000 to 200,000, and particularly from 10,000 to 50,000.

For example, vinylpyridine polymers and vinylpyridinium cation polymers as disclosed in U.S. Pat. Nos. 2,548,564, 2,484,430, 3,148,061 and 3,756,814, etc., polymer mordants capable of cross-linking with gelatin as disclosed in U.S. Pat. Nos. 3,625,694, 3,859,096 and 4,128,538, British Pat. No. 1,277,453, etc., aqueous sol type mordants as disclosed in U.S. Pat. Nos. 3,958,995, 2,721,852 and 2,798,063, Japanese Patent Application (OPI) Nos. 115228/79, 145529/79 and 126027/79, etc., water-insoluble mordants as disclosed in U.S. Pat. No. 3,898,088, etc., reactive mordants capable of forming cobalent bonds with dyes used as disclosed in U.S. Pat. No. 4,168,976 (Japanese Patent Application (OPI) No. 137333/79), etc., and mordants disclosed in U.S. Pat. Nos. 3,709,690, 3,788,855, 3,642,482, 3,488,706, 3,557,066, 3,271,147 and 3,271,148, Japanese Patent Application (OPI) Nos. 71332/75, 30328/78, 155528/77, 125/78 and 1024/78, etc., can be illustrated.

In addition, mordants disclosed in U.S. Pat. Nos. 2,675,316 and 2,882,156 can be used.

The dye fixing layer (II) can have a white reflective layer. For example, a layer of titanium dioxide dispersed in gelatin can be provided on the mordant layer on a transparent support. The layer of titanium dioxide forms a white opaque layer, by which reflection color images of the transferred color images which can be observed through the transparent support is obtained.

Typical dye fixing material used in the present invention is obtained by mixing the polymer containing ammonium salt groups with gelatin and applying the mixture to a transparent support.

The transfer of dyes from the light-sensitive layer to the dye fixing layer can be carried out using a dye transfer assistant. Examples of useful dye transfer assistant include water and an alkaline aqueous solution containing sodium hydroxide, potassium hydroxide and an inorganic alkali metal salt. Further, a solvent having a low boiling point such as methanol, N,N-dimethylformamide, acetone, diisobutyl ketone, etc., and a mixture of such a solvent having a low boiling point with water or an alkaline aqueous solution can be used. The dye transfer assistant can be employed by wetting the image receiving layer with the transfer assistant or by incorporating it in the form of water of crystallization or microcapsules into the material.

The present invention will be explained in greater detail with reference to the following examples, but the present invention should not be construed as being limited thereto. "Percent" in the examples means "percent by weight".

The synthesis examples of dye releasing compounds used in the examples are described in European Patent Application (OPI) No. 76,492 in detail.

EXAMPLE 1

First, a method of preparing a silver iodobromide emulsion is described.

40 g of gelatin and 26 g of potassium bromide were dissolved in 3,000 ml of water and the solution was stirred while maintaining the temperature at 50° C. A solution containing 34 g of silver nitrate dissolved in 20 ml of water was added to the above-described solution over a period of 10 minutes. Then, a solution containing 3.3 g of potassium iodide dissolved in 100 ml of water was added for a period of 2 minutes. By controlling the pH of the silver iodobromide emulsion thus prepared precipitate was formed and the excess salts were removed. The pH of the emulsion was then adjusted to 6.0 and 400 g of the silver iodobromide emulsion was obtained.

In the following, a method of preparing a gelatin dispersion of a dye releasing redox compound containing the compound according to the present invention is described.

A mixture of 5 g of Magenta Dye Releasing Redox Compound (I) described below, 0.5 g of 2-ethylhexyl sodium sulfosuccinate as a surface active agent, 5 g of Compound (22) according to the present invention and 20 ml of ethyl acetate was heated at about 60° C. to form a uniform solution.

Magenta Dye Releasing Compound (I)

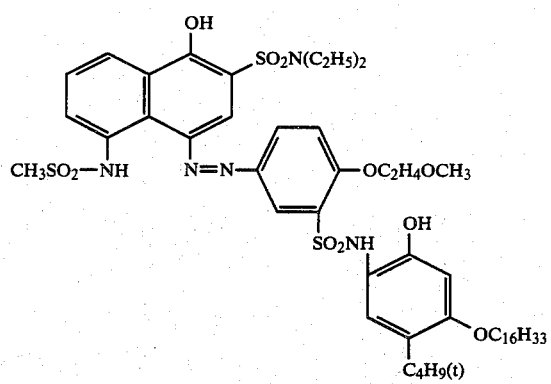

The solution was mixed with 100 g of a 10% aqueous solution of lime-processed gelatin with stirring and then dispersed using a homogenizer at 10,000 rpm for 10 minutes. The dispersion thus prepared is designated a dispersion of dye releasing redox compound containing the compound according to the present invention.

In the following, a method of preparing a light-sensitive material is described.

| | | |
|---|---|---|
| (a) | The light-sensitive silver iodobromide emulsion | 25 g |
| (b) | The dispersion of dye releasing redox compound containing the compound according to the present invention | 33 g |
| (c) | A 10% ethanol solution of guanidine trichloroacetate | 15 ml |
| (d) | A 5% aqueous solution of a compound having the following structure: | 5 ml |

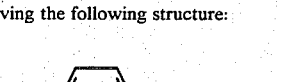

| | | |
|---|---|---|
| (e) | A 10% aqueous solution of dimethylsulfamide | 3 ml |
| (f) | Water | 5 ml |

The above-described components (a) to (f) were mixed and dissolved. The solution was coated on a polyethylene terephthalate film at a wet thickness of 30 μm. On the layer thus formed was coated a 3% aqueous solution of gelatin at a wet thickness of 30 μm to form a protective layer. The light-sensitive material thus prepared is designated Sample (A).

For comparison, Samples (B) and (B') were prepared in the same manner as described for Sample (A) except that Comparison Compounds (1) and (2) described below were used respectively in place of Compound (22) according to the present invention in the dispersion of dye releasing redox compound containing the compound according to the present invention.

Comparison Compound (1)

$(C_4H_9O)_3P=O$

Comparison Compound (2)

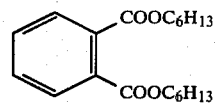

Both Comparison Compounds (1) and (2) above are well known as dispersing agents.

These samples were dried and exposed imagewise at 2,000 lux for 10 seconds using a tungsten lamp and then uniformly heated for 30 seconds on a heat block which had been heated at 130° C.

In the following, a method of preparing a dye fixing material is described.

10 g of copolymer of methyl acrylate and N,N,N-trimethyl-N-vinylbenzyl ammonium chloride (a mol ratio of methyl acrylate and vinylbenzyl ammonium chloride being 1:1) was dissolved in 200 ml of water and the solution was uniformly mixed with 100 g of a 10% aqueous solution of lime-processed gelatin. The mixture solution was uniformly coated on a paper support laminated with polyethylene containing titanium dioxide dispersed therein at a wet thickness of 90 μm and dried to prepare a dye fixing material having a mordant layer.

The dye fixing material was soaked in water and superposed on the heated light-sensitive material described above so as to bring into contact with each of the surface layers, and they were heated on a heat block at 80° C. for 6 seconds. The dye fixing material was peeled apart from the light-sensitive material thereby negative magenta color images were obtained on the dye fixing material. The maximum density ($D_{max}$) and the fog density ($D_{min}$) to green light of the negative images were measures using a Macbeth reflective densitometer (RD-519). The results are shown in Table 1 below.

Further, Samples (A), (B) and (B') were preserved at room temperature under light-shielding condition for 3 months and then exposed to light, heated and transferred in the same manner as described for the samples just after preparation. The densities to green light of the negative images thus obtained were measured using a Macbeth reflective densitometer (RD-519) and the results shown in Table 1 below were obtained.

TABLE 1

| Sample | Just after Preparation | | After Preservation for 3 Months | |
|---|---|---|---|---|
| | Dmax | Dmin | Dmax | Dmin |
| (A) | 1.82 | 0.22 | 2.00 | 0.41 |
| (B) | 2.26 | 0.30 | 2.35 | 2.28 |
| (B') | 2.08 | 0.27 | 2.34 | 1.89 |

From the results shown in Table 1 above, it is apparent that the occurrence of fog and the change in the maximum density are restrained and thus the stability of the light-sensitive material with the passage of time is improved by the presence of the compound according to the present invention.

EXAMPLE 2

In the following, an example in which silver benzotriazole as an organic silver salt oxidizing agent is used is described.

A silver benzotriazole emulsion was prepared in the manner as described below.

28 g of gelatin and 13.2 g of benzotriazole were dissolved in 3,000 ml of water and the solution was stirred while maintaining at 40° C. A solution containing 17 g of silver nitrate dissolved in 100 ml of water was added to the above described solution for a period of 2 minutes. By controlling a pH of the silver benzotriazole emulsion thus prepared to precipitate and the excess salts were removed. The pH of the emulsion was then adjusted to 6.0 and 400 g of the silver benzotriazole emulsion was obtained.

Using the silver benzotriazole emulsion thus prepared, a light-sensitive material was prepared in the following manner.

| (a) | A silver iodobromide emulsion (same as described in Example 1) | 24 g |
| (b) | The silver benzotriazole emulsion | 2 g |
| (c) | A dispersion* | 33 g |
| (d) | A 10% ethanol solution of guanidine trichloroacetate | 16 ml |
| (e) | A 5% aqueous solution of a compound having the following structure: | 5 ml |

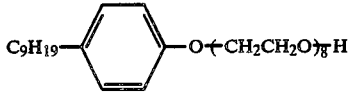

| (f) | A 10% aqueous solution of dimethylsulfamide | 4 ml |
| (g) | Water | 5 ml |

*Dispersion prepared in the same manner as described for the dispersion used in Example 1 except using the compound shown in Table 2 below in place of Compound (22) according to the present invention.

The above-described components (a) to (g) were mixed and dissolved. The solution was coated on a polyethylene terephthalate film at a wet thickness of 30 μm and dried. On the layer thus formed was coated a 3% aqueous solution of gelatin at a wet thickness of 30 μm to form a protective layer. Thus, Samples (C) to (H) were prepared which were the same as the light-sensitive material as described above except using the dispersion of dye releasing redox compound containing the compound according to the present invention as shown in Table 2 below. Further, Sample (I) was prepared using Comparison Compound (1) in place of the compound according to the present invention

TABLE 2

| Sample | Compound | Dye Releasing Redox Compound* |
|---|---|---|
| (C) | (24) [Present Invention] | (II) |
| (D) | (26) [Present Invention] | (II) |
| (E) | (12) [Present Invention] | (II) |
| (F) | (28) [Present Invention] | (II) |
| (G) | (27) [Present Invention] | (II) |
| (H) | (31) [Present Invention] | (II) |
| (I) | Comparison Compound (1) | (II) |

*Dye Releasing Redox Compound (II):

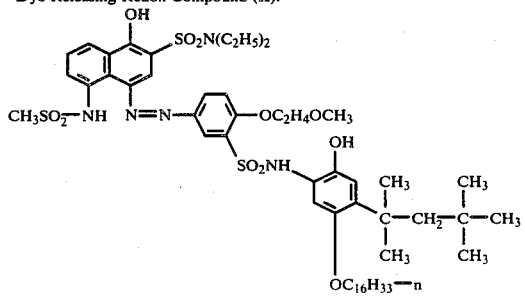

Samples (C) to (I) were subjected to imagewise exposure to light, heating and transferring in the same manner as described in Example 1, just after preparation of the samples and after the preservation in a thermal vessel at 50° C. for 2 days. The reflective density to green light of each sample was measured in the same manner as described in Example 1. The results thus obtained are shown in Table 3 below.

TABLE 3

| Sample | Just after Preparation | | After Preservation at 50° C. for 2 Days | |
|---|---|---|---|---|
| | Dmax | Dmin | Dmax | Dmin |
| (C) | 1.93 | 0.17 | 2.07 | 0.32 |
| (D) | 1.75 | 0.24 | 1.84 | 0.48 |
| (E) | 1.83 | 0.20 | 1.97 | 0.41 |
| (F) | 1.66 | 0.29 | 1.94 | 0.99 |
| (G) | 1.87 | 0.33 | 1.95 | 1.10 |
| (H) | 1.82 | 0.19 | 1.97 | 0.32 |
| (I) | 2.27 | 0.30 | 2.39 | 2.26 |

From the results shown in Table 3 above, it is apparent that the occurrence of fog during preservation is restrained and thus the stability of the light-sensitive material with the passage of time is improved by the presence of the compound according to the present invention.

EXAMPLE 3

Samples (J) to (O) were prepared in the same manner as described in Example 2 except using the dye releasing redox compounds shown in Table 4 below in place of Dye Releasing Redox Compound (II), and further in Samples (K), (M) and (O), Comparison Compound (1) was used in place of the compound according to the present invention.

TABLE 4

| Sample | Compound | Dye Releasing Redox Compound (hue) |
|---|---|---|
| (J) | (24) [Present Invention] | (III) (yellow) |
| (K) | Comparison Compound (1) | (III) (yellow) |
| (L) | (24) [Present Invention] | (IV) (magenta) |
| (M) | Comparison Compound (1) | (IV) (magenta) |
| (N) | (24) [Present Invention] | (V) (cyan) |

TABLE 4-continued

| Sample | Compound | Dye Releasing Redox Compound (hue) |
|---|---|---|
| (O) | Comparison Compound (1) | (V) (cyan) |

Dye Releasing Redox Compound (III):

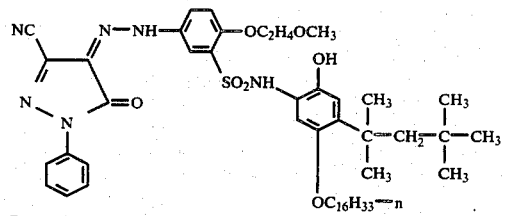

Dye Releasing Redox Compound (IV):

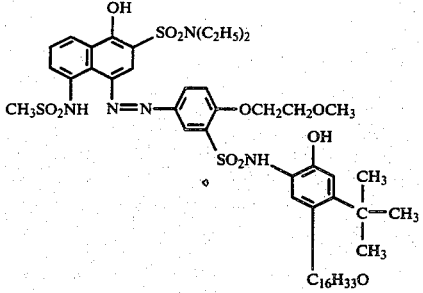

Dye Releasing Redox Compound (V):

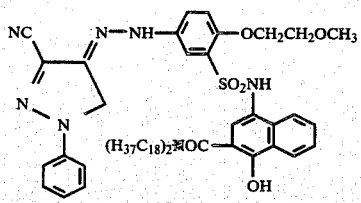

Samples (J) to (O) were subjected to imagewise exposure to light, heating and transferring in the same manner as described in Example 1, just after preparation of the samples and after the preservation in a thermal vessel at 50° C. for 2 days. The reflective density to blue light for Samples (J) and (K), green light for Samples (L) and (M) and red light for Samples (N) and (O) was measured in the same manner as described in Example 1. The results thus obtained are shown in Table 5 below.

TABLE 5

| Sample | Just after Preparation | | After Preservation at 50° C. for 2 Days | |
|---|---|---|---|---|
| | Dmax | Dmin | Dmax | Dmin |
| (J) | 1.81 | 0.18 | 1.95 | 0.29 |
| (K) | 2.02 | 0.25 | 2.28 | 1.08 |
| (L) | 2.07 | 0.22 | 2.19 | 0.36 |
| (M) | 2.28 | 0.31 | 2.37 | 2.06 |
| (N) | 1.96 | 0.32 | 2.12 | 0.65 |
| (O) | 2.14 | 0.33 | 2.32 | 0.94 |

From the results shown in Table 5 above, it is apparent that the occurrence of fog during preservation in restrained and thus the stability of the light-sensitive material with the passage of time is improved by the presence of the compound according to the present invention with respect to Dye Releasing Redox Compound (III), Dye Releasing Redox Compound (IV) and the Dye Releasing Redox Compound (V).

EXAMPLE 4

Samples (P), (Q) and (R) were prepared in the same manner as described in Example 2 except using the compounds according to the present invention and the dye releasing redox compounds shown in Table 6 below respectively in place of the compound according to the present invention and the dye releasing redox compound used in Examples 2.

TABLE 6

| Sample | Compound | Dye Releasing Redox Compound |
|---|---|---|
| (P) | (2) [Present Invention] | (I) |
| (Q) | (18) [Present Invention] | (I) |
| (R) | (23) [Present Invention] | (I) |

Samples (P), (Q) and (R) were subjected to imagewise exposure to light, heating and transferring in the same manner as described in Example 2, just after preparation of the samples and after the preservation in a thermal vessel at 50° C. for 2 days. The results thus obtained indicated that the occurrence of fog with the passage of time was restrained in all samples.

While the invention has been described in detail and with reference to specific embodiment thereof, it will be apparent to one skilled in the art that various changes and modifications can be made therein without departing from the spirit and scope thereof.

What is claimed is:

1. A method of forming an image comprising heating a light-sensitive material having at least a light-sensitive silver halide, a binder and a dye releasing redox compound which is capable of reducing the light-sensitive silver halide and is capable of reacting with the light-sensitive silver halide by heating to release a hydrophilic dye on a support, under the condition substantially free from water after or simultaneously with imagewise exposure, in the presence of a compound represented by the general formula (A) described below to form imagewise a mobile dye

wherein R represents an alkyl group, a cycloalkyl group, an aryl group or an aralkyl group; $R^1$ represents an alkyl group, a cycloalkyl group, an aryl group or an aralkyl group; $R^2$ represents an alkyl group, an aryl group, an aralkyl group, a halogen atom or a group of $R^1NH$; Z represents an atomic group necessary to form a carbon ring condensed to the benzene ring; n represents 0, 1 or 2; m represents 0 or an integer from 1 to 7 and m+n is not more than 7; l represents 0 or 1; and each of $R^1$ and $R^2$ may be the same or different when m or n represents 2 or more, respectively.

2. A method of forming an image as claimed in claim 1, wherein the alkyl group represented by R, $R^1$ or $R^2$ is an alkyl group having from 1 to 20 carbon atoms.

3. A method of forming an image as claimed in claim 1, wherein the alkyl group represented by R, $R^1$ or $R^2$ is a group represented by the following formula:

$$C_kH_{2k+1}-$$

wherein k is an integer from 1 to 20.

4. A method of forming an image as claimed in claim 1, wherein the alkyl group represented by R, $R^1$ or $R^2$ is an alkyl group substituted with an alkoxy group having from 1 to 20 carbon atoms or a substituted alkoxy group.

5. A method of forming an image as claimed in claim 1, wherein the cycloalkyl group represented by R or $R^1$ is a cycloalkyl group having from 3 to 20 carbon atoms.

6. A method of forming an image as claimed in claim 1, wherein the cycloalkyl group represented by R or $R^1$ is a group represented by the following formula:

$$C_kH_{2k-p}-$$

wherein k is an integer from 3 to 20; and p is 1, 3, 5 or 7.

7. A method of forming an image as claimed in claim 1, wherein the aryl group represented by R, $R^1$ or $R^2$ is an aryl group having from 6 to 30 carbon atoms.

8. A method of forming an image as claimed in claim 1, wherein the aralkyl group represented by R, $R^1$ or $R^2$ is an aralkyl group having from 7 to 30 carbon atoms.

9. A method of forming an image as claimed in claim 7, wherein the aryl group is an aryl group substituted with an alkyl group, an alkoxy group, an alkylamino group, an arylamino group, an arylamino group or an acyloxy group.

10. A method of forming an image as claimed in claim 8, wherein the aralkyl group is an aralkyl group wherein the aryl moiety is substituted with an alkyl group, an alkoxy group, an alkylamino group, an arylamino group or an acyloxy group.

11. A method of forming an image as claimed in claim 1, wherein the compound represented by the general formula (A) is present in the light-sensitive material.

12. A method of forming an image as claimed in claim 11, wherein the compound represented by the general formula (A) is incorporated into a light-sensitive emulsion layer.

13. A method of forming an image as claimed in claim 11, wherein the compound represented by the general formula (A) is incorporated into an intermediate layer or a surface protective layer.

14. A method of forming an image as claimed in claim 1, wherein the compound represented by the general formula (A) is present in a dye fixing material.

15. A method of forming an image as claimed in claim 14, wherein the compound represented by the general formual (A) is incorporated into a layer containing a mordant.

16. A method of forming an image as claimed in claim 1, wherein the compound represented by the general formula (A) is present in an amount ranging from 0.01 time to 20 times by weight based on the dye releasing redox compound.

17. A method of forming an image as claimed in claim 1, wherein the compound represented by the general formula (A) is present in an amount ranging from 0.001 g/m² to 5 g/m².

18. A method of forming an image as claimed in claim 1, wherein the heating is carried out at a temperature of 80° C. or higher.

19. A method of forming an image as claimed in claim 1, wherein the heating is carried out in the presence of an organic silver salt oxidizing agent.

20. A method of forming an image as claimed in claim 1, the method further comprising transferring the imagewise mobile dye to a dye fixing layer.

21. A method of forming an image as claimed in claim 1, wherein the heating is carried out in the presence of a dye releasing activator.

22. A light-sensitive material comprising a support having thereon at least a light-sensitive silver halide, a binder, a dye releasing redox compound which is capable of reducing the light-sensitive silver halide and is capable of reacting with the light-sensitive silver halide by heating to release a hydrophilic dye and a compound represented by the general formula (A)

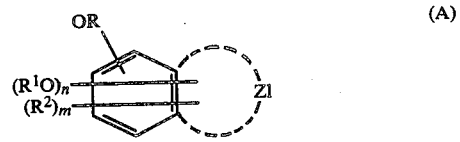

wherein R represents an alkyl group, a cycloalkyl group, an aryl group or an aralkyl group; $R^1$ represents an alkyl group, a cycloalkyl group, an aryl group or an aralkyl group; $R^2$ represents an alkyl group, an aryl group, an aralkyl group, a halogen atom or a group of $R^1NH$; Z represents an atomic group necessary to form a carbon ring condensed to the benzene ring; n represents 0, 1 or 2; m represents 0 or an integer from 1 to 7 and m+n is not more than 7; l represents 0 or 1; and each of $R^1$ and $R^2$ may be the same or different when m or n represents 2 or more, respectively.

23. A light-sensitive material as claimed in claim 22, wherein the compound represented by the general formula (A) is present in a light-sensitive emulsion layer.

24. A light-sensitive material as claimed in claim 22, wherein the compound represented by the general formula (A) is present an intermediate layer or a surface protective layer.

25. A light-sensitive material as claimed in claim 22, wherein the compound represented by the general formual (A) is present in an amount ranging from 0.01 time to 20 times by weight based on the dye releasing redox compound.

* * * * *